United States Patent [19]

Morris et al.

[11] Patent Number: 4,855,515
[45] Date of Patent: Aug. 8, 1989

[54] PROCESS FOR THE PRODUCTION OF NEOPENTYL GLYCOL

[75] Inventors: Don L. Morris; Billy W. Palmer; Thomas W. McAninch, all of Longview, Tex.

[73] Assignee: Eastman Kodak Company, Rochester, N.Y.

[21] Appl. No.: 84,716

[22] Filed: Aug. 12, 1987

[51] Int. Cl.$^4$ .............. C07C 29/14; C07C 31/20
[52] U.S. Cl. .................. 568/862; 568/881; 568/885
[58] Field of Search ............ 568/862, 885, 881

[56] References Cited

U.S. PATENT DOCUMENTS

| | | | |
|---|---|---|---|
| 2,109,844 | 3/1938 | Lazier | 568/885 |
| 2,461,220 | 2/1949 | Lorand et al. | 260/637 |
| 2,549,416 | 4/1951 | Brooks | 260/638 |
| 2,761,881 | 9/1956 | Rosin | 260/635 |
| 2,778,858 | 1/1957 | Meinhofer | 260/635 |
| 2,786,083 | 3/1957 | Wyler | 260/635 |
| 2,811,562 | 10/1957 | Hagemeyer, Jr. | 260/602 |
| 2,865,819 | 12/1958 | Hagemeyer, Jr. | 202/42 |
| 2,895,996 | 7/1959 | Wright, Jr. et al. | 260/637 |
| 3,067,260 | 12/1962 | Nobis et al. | 260/637 |
| 3,077,500 | 2/1963 | Heinz et al. | 260/594 |
| 3,088,982 | 5/1963 | Feldman et al. | 260/637 |
| 3,168,579 | 2/1965 | Boswell, Jr. et al. | 260/635 |
| 3,340,312 | 9/1967 | Duke, Jr. et al. | 260/635 |
| 3,462,500 | 8/1969 | Tummes et al. | 260/643 |
| 3,483,264 | 12/1969 | Tsao | 260/637 |
| 3,504,042 | 3/1970 | Shimono et al. | 260/635 |
| 3,542,878 | 11/1970 | Swift | 260/586 |
| 3,652,458 | 3/1972 | Gobron et al. | 252/454 |
| 3,808,280 | 4/1974 | Merger et al. | 260/635 |
| 3,862,215 | 1/1975 | Merger et al. | 260/484 |
| 3,876,706 | 4/1975 | Levanevsky et al. | 260/602 |
| 3,886,219 | 5/1975 | Reich | 260/638 |
| 3,920,760 | 11/1975 | Heinz | 260/635 A |
| 3,935,274 | 1/1976 | Jacobsen et al. | 260/602 |
| 3,939,216 | 2/1976 | Wright | 260/635 |
| 3,975,450 | 8/1976 | Palmer et al. | 260/635 |
| 4,032,578 | 6/1977 | Savini | 260/601 |
| 4,036,888 | 7/1977 | Couderc | 260/602 |
| 4,038,329 | 7/1977 | Palmer et al. | 260/637 |
| 4,052,467 | 10/1977 | Mills et al. | 260/638 B |
| 4,094,914 | 6/1978 | Rottig et al. | 568/862 |
| 4,096,192 | 6/1978 | Bhatia et al. | 568/866 |
| 4,097,540 | 6/1978 | Immel et al. | 568/862 |
| 4,113,662 | 9/1978 | Wall | 252/473 |
| 4,165,339 | 8/1979 | Reichle | 260/586 |
| 4,181,810 | 1/1980 | Immel et al. | 568/807 |
| 4,182,659 | 1/1980 | Anwer et al. | 203/18 |
| 4,250,337 | 2/1981 | Hausen et al. | 568/853 |
| 4,298,766 | 11/1981 | Broecker et al. | 568/862 |
| 4,386,219 | 5/1983 | Merger et al. | 568/853 |
| 4,393,251 | 7/1983 | Broecker et al. | 568/811 |

FOREIGN PATENT DOCUMENTS

| | | |
|---|---|---|
| 0008767 | 3/1980 | European Pat. Off. |
| 138607 | 11/1976 | Japan |
| 6405068 | 11/1964 | Netherlands |
| 783458 | 9/1957 | United Kingdom |
| 988316 | 4/1965 | United Kingdom |
| 1219162 | 1/1971 | United Kingdom |

OTHER PUBLICATIONS

Chem. Zeitung, 100(12), 504 (1976).

*Primary Examiner*—Donald B. Moyer
*Assistant Examiner*—Karen E. Kulesza
*Attorney, Agent, or Firm*—Thomas R. Savitsky; William P. Heath, Jr.; Mark A. Montgomery

[57] ABSTRACT

A method for producing neopentyl glycol is described using tertiaryamines as a catalyst for the condensation of isobutyraldehyde and formaldehyde followed by hydrogenation of the resulting reaction mixture using a manganese oxide promoted copper chromite catalyst.

7 Claims, 3 Drawing Sheets

ALDOL REACTOR SECTION

P   PUMP
$R_1$   RECIRCULATION ALDOL REACTOR
$R_2$   RECIRCULATION ALDOL REACTOR
$T_1$   ISOBUTYRALDEHYDE FEED TANK
$T_2$   FORMALDEHYDE FEED TANK
$T_3$   TRIETHYLAMINE FEED TANK (MAKE-UP)
$T_4$   ISOBUTYRALDEHYDE - TRIETHYLAMINE RECYCLE
   (FROM D-3, OVERHEAD)

HYDROGENATION SECTION

- $B_1$ FIRST STAGE HYDROGENATION BED
- $B_2$ SECOND STAGE HYDROGENATION BED
- P PUMP
- $T_5$ RECYCLE TANK
- $T_6$ RECYCLE TANK
- $V_1$ VAPOR LIQUID SEPARATOR
- $V_2$ VAPOR LIQUID SEPARATOR

PROCESS FOR THE PRODUCTION OF NEOPENTYL GLYCOL

FIELD OF THE INVENTION

This invention relates to a method for producing neopentyl glycol using tertiaryamines as a catalyst for the condensation of isobutyraldehyde and formaldehyde followed by hydrogenation of the resulting reaction mixture using a manganese oxide promoted copper chromite catalyst.

BACKGROUND OF THE INVENTION

Neopentyl glycol,2,2-dimethyl-1,3-dihydroxypropane, is a diol of substantial value in the commercial chemical arts useful in a variety of formulations in lubricants and adhesives, coatings, plastics and fibers. As a key component in many chemical products, the cost and purity of neopentyl glycol is a key determinant in the eventual competitiveness of the products produced therefrom. Accordingly, those skilled in the chemical arts applicable to neopentyl glycol regularly search for improvements in the process for the production of the diol to advance the technology and usefulness of the products produced.

Due to the usefulness of neopentyl glycol and to certain complexities intrinsic to its manufacture the chemical has been the subject of a substantial number of investigations directed toward improved manufacturing processes and consequently, the prior art is crowded. Although the basic chemistry of the synthesis of neopentyl glycol appear quite straight forward, when incorporated in a process directed toward maximum economic yield challenging problems are presented.

The basic reaction for the most common processes for the manufacture of neopentyl glycol is represented by the equation:

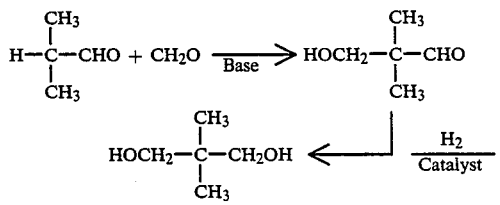

wherein isobutyraldehyde and formaldehyde are allowed to react through aldol condensation in the presence of a basic catalyst to yield 2,2-dimethyl-3-hydroxypropanal (hydroxypivaldehyde). This intermediate is then catalytically hydrogenated to produce neopentyl glycol.

The synthesis of neopentyl glycol has been the subject of reviews in the chemical literature, in particular the review by Cornils and Feischtinger in Chem Zeitung, 100 (12) 504 (1976). Catalysts employed to affect the aldol condensation have included alkali hydroxides, alkaline earth metal hydroxides, alkali carbonates, tertiary amines and basic ion exchangers. Of these aldol catalysts, the use of alkali hydroxides, alkali carbonates and tertiary amines has received the most study in the literature. The object of the search for improved catalysts is the reduction or elimination of side reactions that compete with the desired aldol condensation and produce impurities in the reaction mixture requiring additional process steps for their removal. The competing side reactions are due to Cannizzaro and Tischenko reactions where, in the former, two moles of aldehyde react to produce a mole of alcohol and a mole of carboxylic acid and, in the later, two moles of aldehyde react to form the corresponding ester. To the extent these competing reactions occur, the yield and purity of the desired product are not satisfactory and processes based on this overall reaction scheme, such as U.S. Pat. No. 2,400,724, are not generally considered economically viable.

To moderate these competing reactions which occur particularly in the presence of alkali hydroxides sodium carbonate has been used as described in U.S. Pat. No. 2,811,562. Although improvements have been found for aldol catalysts that reduce side reactions, these catalysts may complicate the subsequent hydrogenation step by requiring separation of the intermediate hydroxypivaldehyde before hydrogenation or may dictate the selection of a hydrogenation catalyst of intermediate activity, thereby reducing the final yield of neopentyl glycol. Efforts to resolve this problem have been described in UK Pat. No. 1,017,618 as well as UK Pat. No. 1,048,530 wherein 2,2-dimethyl-3-hydroxypropanal is hydrogenated simultaneously with isobutyraldehyde in the presence of a copper/chromium oxide catalyst. This process is reported to lead to the formation of appreciable quantities of a large number of by-products.

The use of tertiary amines as the aldol catalyst for the condensation of formaldehyde and isobutyraldehyde is also described in Dutch Pat. No. 6,405,068 and in U.S. Pat. No. 3,808,280. U.S. Pat. No. 3,808,280 claims the use of triethylamine as the aldol catalyst and the subsequent use of catalysts containing at least one of cobalt, copper, manganese and nickel to convert the hydroxypivaldehyde to neopentyl glycol and teaches a mixture of these metals is the preferred catalyst. The use of triethylamine and a copper-containing hydrogenation catalyst is claimed; however, it is indicated that copper chromite would be a poor hydrogenation catalyst because of decomposition of hydroxypivaldehyde to produce excessive by-products and lowered yield of neopentyl glycol. Further, the hydrogenation step as described is U.S. Pat. No. 3,808,280 is conducted between 1,500 and 4,000 psig.

OBJECT OF THE INVENTION

It is an object of this invention to provide a new process for the manufacture of 2,2-dimethyl-1,3-dihydroxypropane in high yields and purity in a simpler and more economical manner.

It is another object of this invention to provide a new low pressure process for the manufacture of 2,2-dimethyl-1,3-dihydroxypropane.

Yet another object of this invention is to provide a continuous new process for the manufacture of neopentyl glycol that does not require the separation of the intermediate, hydroxypivaldehyde.

Yet another object of this invention is to provide a new low pressure, continuous process for the manufacture of neopentyl glycol wherein the quantity of aldol condensation by-products is low.

Yet another object of this invention is to provide a new process for the manufacture of neopentyl glycol incorporating a hydrogenation step employing a highly reactive and specific catalyst with long catalytic life.

SUMMARY OF THE INVENTION

These objects of the present invention are achieved by an improvement in the production of neopentyl glycol wherein isobutyraldehyde and formaldehyde is condensed in the presence of a tertiary amine catalyst to provide a reaction mixture comprising hydroxypivaldehyde and subjecting the reaction mixture to hydrogenation. This improvement of the invention involves employing as the hydrogenation catalyst a manganese oxide-promoted copper oxide/copper chromite catalyst. Furthermore, it has been surprisingly found that the hydrogenation step in the production of neopentyl glycol can be conducted at hydrogen pressures substantially lower than those employed in the prior art. Compared to the prior art processes, substantial advantage accrues to the process of this invention due to its ability to operate in a continuous manner at hydrogenation pressures more than 50 atmospheres lower. This advantage affects virtually all process cost factors including equipment size, control design, safety and reliability; thereby providing a substantial advancement in the field of neopentyl glycol manufacturing.

The advantage enjoyed through low pressure operation of the process of this invention comes at no disadvantage in product yield or quality vis-a-vis the prior art. Indeed, yields of neopentyl glycol in excess of 90% have been produced by the process of this invention with no discernible disadvantage in by-product or tractabiity. By-products are typical of those found in the art as practiced in other processes and constitute primarily isobutanol and sodium salts of carboxylic acids. Their separation is affected smoothly employing commonly applicable separation techniques.

In general, the process of this invention is conducted by the simultaneous addition of isobutyraldehyde, formaldehyde and triethylamine to a recirculating reactor in a mole ratio of about 1.1/1.0/0.04. The aldol condensation is allowed to proceed for approximately one hour at elevated temperatures typically about 90° C. The reaction mixture containing crude condensation product, hydroxypivaldehyde, is separated by distillation where unreacted starting materials are returned to the recirculating reactor. The aldol product from the isobutyraldehyde recovery column is then fed to a hydrogenation reactor operated at about 150 to 220° C., preferably about 170° C., under about 300 to 1500 psig, preferably under about 300 to 1000 psig, and most preferably about 500 psig, of hydrogen where the hydrogenation is conducted in the presence of the maganese promoted copper chromite catalyst. The hydrogenation product is separated, for instance, by distillation to provide neopentyl glycol in a yield of 90.6% based on isobutyraldehyde.

The manganese oxide-promoted copper chromite catalyst employed in this invention may contain between 45–47% by weight copper oxide (CuO), 45–47% by weight copper chromite ($CuCr_2O_4$) and 2–8% by weight manganese oxide ($MnO_2$). The catalyst is commercially available as G-89 from United Catalyst, Incorporated and is identified as a manganese oxide-promoted $CuO:CuCr_2O_4$.

The selection of tertiary amines as catalysts for effecting the aldol condensation between importance both in controlling competing side reactions to the aldol condensation and the fact that the tertiary amine catalyst need not be separated from the aldol reaction mixture before hydrogenating the hydroxypivaldehyde, provided such hydrogenation is conducted employing the manganese promoted copper chromite catalyst disclosed herein. While triethylamine is a preferred catalyst for aldol condensation, other tertiary amines may be employed including trialkylamines such as methyldiethylamine, ethyldimethylamine, tripropylamine, dimethyltertiary butylamine, and the like. Similarly, aromatic amines derived from aniline and its derivatives may be employed such as phenyldimethylamine, phenyldiethylamine, methyldiphenylamine, and the like. Tertiary amines wherein the nitrogen moiety is included as part of a hetrocyclic ring may also be used effectively as aldol condensation catalysts. Such amines may include methylpiperidine, dimethylpiperazine, methylmorpholine, methylthiamorpholine, and the like. The amount of tertiary amine used as aldol catalyst should in all cases be suitable to accomplish the aldol condensation and, in general, is limited to an amount between 0.1 to 10 weight percent based on the isobutyraldehyde. Preferably, the concentration of tertiary amine catalyst is about 3 weight percent.

It is a most important feature of this invention that subsequent hydrogenation of the aldol condensation reaction mixture is conducted without the need to separate the aldol catalyst from the reaction mixture or to separate by-products of the aldol condensation reaction. Further, the hydrogenation is conducted at low pressures in the presence of the hydrogenation catalyst disclosed herein. Of course, very high pressure hydrogenations may be conducted as well but in those cases the economic advantages that accrue to low pressure hydrogenation are lost with no compensatory increase in yield or quality of the desired product, neopentyl glycol.

A further distinguishing aspect of this invention relating specifically to the hydrogenation of the aldol reaction mixture to produce neopentyl glycol is that, in the presence of manganese promoted copper chromite hydrogenation catalyst, a favorable weight hourly space velocity can be practiced. Even at hydrogenation pressures as low as 500 psig a weight hourly space velocity (whsv) of 1.0 hour$^{-1}$ to 0.1 hour$^{-1}$ can be maintained. Higher hydrogenation pressures are not required to maintain these favorable space velocities and the favorable yields and process economics for neopentyl glycol obtained therefrom.

It is taught in the art that hydrogenation of hydroxypivaldehyde using a barium-activated catalyst will not be satisfactory, i.e., will lessen the lifetime of the catalyst (see U.S. Pat. 4,250,337). It is, therefore, another distinguishing aspect, and surprising aspect, of the present invention that the hydrogenation of hydroxypivaldehyde process of the present invention proceeds satisfactorily in the presence of about 25 to 38% by weight water, without substantial catalyst degradation.

DETAILED DESCRIPTION OF THE INVENTION

The detailed process for the manufacture of neopentyl glycol embodied in the instant invention is described by reference to the operation of events occuring in the aldol reactor unit and hydrogenation reactor. The process is illustrated schematically in FIGS. 1–3 where FIG. 1 is the aldol reactor section, FIG. 2 is the hydrogenation section and FIG. 3 is the distillation section.

Figure 1:
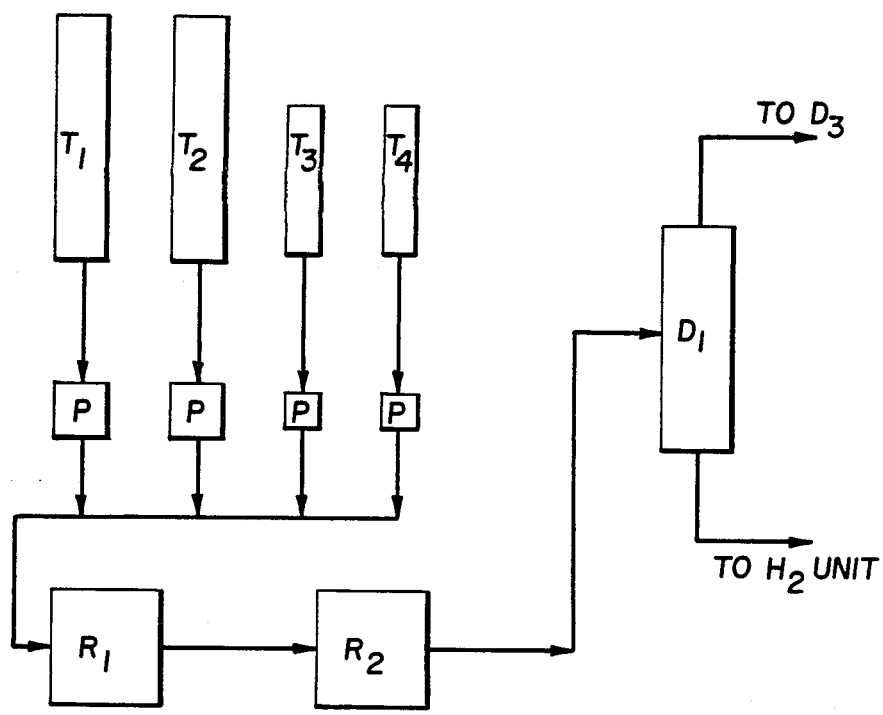
Figure 2:
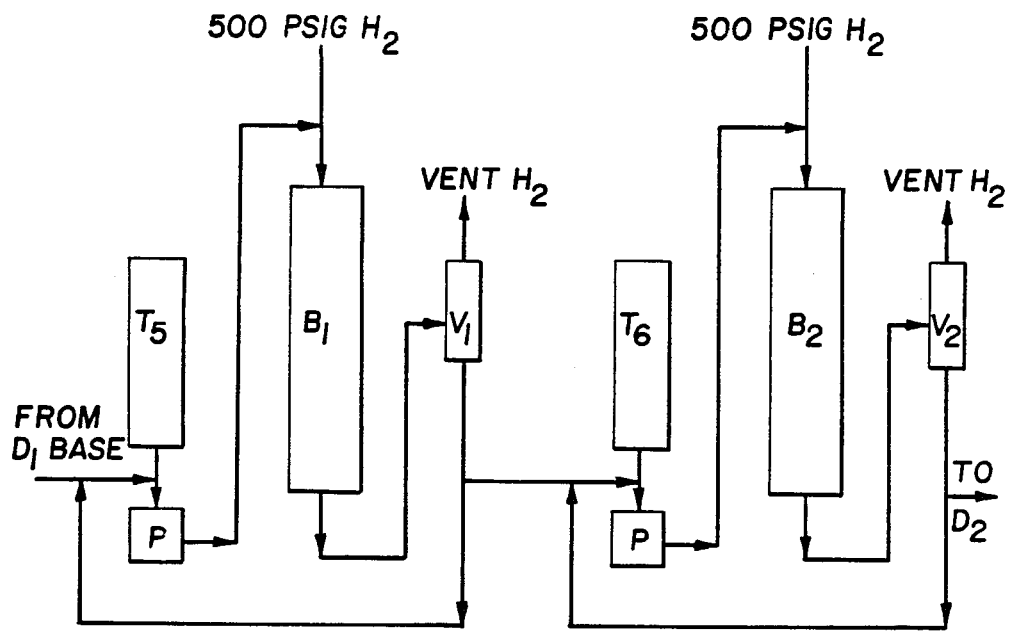

In FIG. 1, T1 through T4 are feed tanks for the reactants and catalyst. R1 and R2 are recirculating aldol reactors and P identifies feed pumps to the reactors. In FIG. 2, a two-stage hydrogenation section is illustrated including a first and second stage hydrogenation bed, B1 and B2, recycle tanks, T5 and T6, for said hydrogenation beds, vapor liquid separators, V1 and V2, and reactor feed pumps, P.

Figure 3:
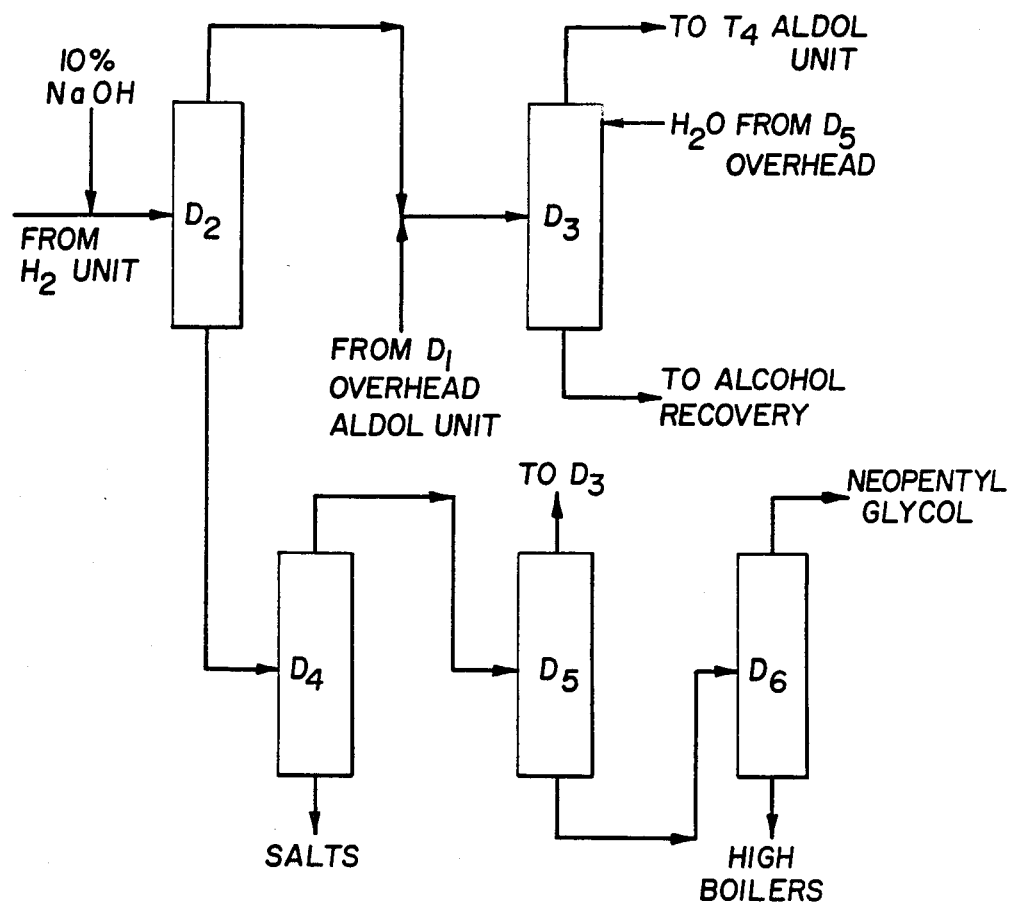

The distillation section shown in FIG. 3 illustrates a series of distillation columns, D2-D6, for removal of low boiling components in D2, extractive distillation in D3 for alcohol recovery and separation of unreacted starting materials, a flash column D4 for salt removal, drying column D5, and a final refining column D6 for neopentyl glycol production and separation of high boilers.

The aldol section, FIG. 1, consists of a feed system for simultaneously adding isobutyraldehyde, 44 percent formaldehyde and triethylamine to a recirculating reactor which is operated at 90° C. under 10 psig pressure. The residence time in the first recirculating reactor is 33 minutes. The rector is operated liquid full and feeds a second recirculating reactor also held at 90° C. under 10 psig pressure. The residence time in the second reactor is 27 minutes. The pressure is maintained by pumping agaist'a control valve which opens at pressure above 10 psig and allows the crude aldol condensation product, hydroxypivaldehyde, to enter a 1-inch by 4-foot Penn State packed distillation column with a midpoint feed (D1). This column recovers any unreacted isobutyraldehyde and triethylamine that has not been converted to salts via the Cannizzaro reaction. The feed mole ratio of isobutyraldehyde, formaldehyde, and triethylamine is maintained at 1.1/1.0/0.04, respectively. The recovered isobutyraldehyde is used in a subsequent extractive distillation (Column D3) for triethylamine recovery described in the distillation section (FIG. 3). The recovered isobutyraldehyde and triethylamine from the extractive distillation (D3) is also fed to the aldol unit. Its composition is typically 60 percent isobutyraldehyde. 20 percent triethylamine, 2.4 percent isobutanol, 9.6 percent methanol, and 6.0 percent water with 1.6 percent other products. The mole ratios described above include this feed stream. Typical feed rates are 500 ml fresh isobutyraldehyde, 100 ml isobutyraldehyde from D3, and 300 ml, 44 percent formaldehyde solution.

Fresh triethylamine (makeup) is added to the aldol unit to maintain at a 2.0 percent concentration in the aldol recirculating reactors. This requires 0.1 pound per 100 pounds of neopentyl glycol produced in the process.

The aldol product taken from the base of the isobutyraldehyde recovery Column D1 is fed to a two-stage trickle bed hydrogenation reactor (Figure 2) which operates at 160° C. to 170° C. under 500 psig of $H_2$. The hydrogenation catalyst is 1/8 by 3/16 inch pellets of United Catalyst, Inc. G-89 copper chromite manganese promoted. The catalyst contains 650 grams of this catalyst. The first bed is operated with a recycle of hydrogenated product of 9 volumes per volume of aldol product feed. The product from the first stage has a typical composition in weight percent of 1.0 percent methanol, 5 percent isobutanol, 4 percent hydroxypivaldehyde, 60.4 percent neopentyl glycol, 0.2 percent trimethyl pentanediol, 0.3 percent $C_9$ ester, 0.1 percent $C_{10}$ acetal, 3.0 percent $C_{10}$-ester, 25 percent $H_2O$, and 1.0 percent triethylamine and triethylammonium salts. The second stage reactor operates at 160° C. to 170° C. at 500 psig of $H_2$ and contains 325 grams of catalyst. This reactor does not have recirculation and produces a product containing 1.1 percent methanol, 5.5 percent isobutanol, 0.2 percent hydroxypivaldehyde, 63.6 percent neopentyl glycol, 0.2 percent trimethyl pentanediol, 0.3 percent $C_9$ ester, 0.1 percent $C_{10}$ acetal, 3.0 percent $C_{10}$ ester, 25 percent $H_2O$, and 1 percent triethylamine and triethylammonium salts. The weight hourly space velocity is 1.0 hour$^{-1}$ through the first hydrogenation bed and 0.1 hour$^{-1}$ through the second bed. Excess hydrogen from both stages of the hydrogenation is vented via a vapor liquid separator to maintain fresh hydrogen to the catalyst beds. The product from the hydrogenation is distilled at atmospheric pressure in a continuous system (Column D2) which is operated at a base temperature of 104° C. The midpoint of the column is fed product from the hydrogenation and a 10 percent sodium hydroxide solution which provides caustic to saponify the esters present in the hydrogenated product and to liberate triethylamine from its carboxylic acid salts. This requires about 0.7 pound of NaOH for 100 pounds of neopentyl glycol produced in the process. The base material from D2 is purified to neopentyl glycol by flash distillation from the salts and drying to remove water before a final refining column. The crude D2 product contains methanol, isobutanol, triethylamine, and water. This material is fed to the midpoint of a 1-inch by 4-foot Oldershaw extractive distillation column (D3). Water from the neopentyl glycol drying column is fed to the top of this column. The recovered isobutyraldehyde and triethylamine from D1 is fed to the middle of this column. The base of the column removes methanol, water and isobutanol from the streams entering from D1 and D2. The overhead from the column removes triethylamine and isobutyraldehyde from recycle to the aldol reactor as described in the aldol section. The recovered yields of products based on isobutyraldehyde is 90.6 percent to neopentyl glycol, 7.1 percent to isobutanol, Na salts of carboxylic acids 2.3 percent. The recovered yields on products based on formaldehyde was 87 percent to neopentyl glycol, 8.3 percent to methanol, and 3.7 percent to salts.

What is claimed is:

1. In the production of neopentyl glycol wherein isobutyraldehyde is condensed with formaldehyde in the presence of a tertiary amine catalyst to produce a reaction mixture comprising hydroxypivaldehyde and subjecting said reaction mixture to hydrogenation in the presence of a hydrogenation catalyst to provide neopentyl glycol, the improvement comprising employing as said hydrogenation catalyst a manganese oxide-promoted copper oxide/copper chromite catalyst.

2. A process according to claim 1 wherein said catalyst comprises between 45 to 47 percent by weight copper oxide, 45 to 47 percent by weight copper chromite, and 2 to 8 percent by weight manganese oxide.

3. A process according to claim 1 wherein the hydrogenating reaction is conducted at a temperature of about 150 to 220° C. and a pressure of about 300 to 1500 psig.

4. A process according to claim 1 wherein the hydrogenating reaction is conducted at a temperature of about 170° C. and a pressure of about 500 psig.

5. A process according to claim 1 wherein the tertiary amine is selected from the group consisting of trialkylamine, diarylalkylamine, dialkylarylamine and heterocyclic tertiary amines in an amount between 0.1 to 10 weight percent based on the isobutyraldehyde.

6. A process according to claim 1 wherein said reaction mixture is aqueous and comprises isobutyraldehyde, triethylamine and formaldehyde wherein said formaldehyde comprises 35-60 weight % aqueous formaldehyde.

7. A process according to claim 1 wherein the hydrogenating reaction is conducted in the presence of about 25 to 38 weight percent water.

* * * * *